United States Patent
Ranch et al.

(10) Patent No.: US 7,057,089 B2
(45) Date of Patent: Jun. 6, 2006

(54) METHODS FOR TRANSFORMING IMMATURE MAIZE EMBRYOS

(75) Inventors: Jerome P. Ranch, West Des Moines, IA (US); Wallace A. Marsh, Ankeny, IA (US)

(73) Assignee: Pioneer Hi-Bred International, Inc., Johnston, IA (US)

(*) Notice: Subject to any disclaimer, the term of this patent is extended or adjusted under 35 U.S.C. 154(b) by 285 days.

(21) Appl. No.: 09/993,080

(22) Filed: Nov. 13, 2001

(65) Prior Publication Data

US 2002/0120961 A1    Aug. 29, 2002

Related U.S. Application Data

(60) Provisional application No. 60/248,427, filed on Nov. 14, 2000.

(51) Int. Cl.
  *C12N 15/05* (2006.01)
  *C12N 15/82* (2006.01)
  *C12N 15/90* (2006.01)

(52) U.S. Cl. .................. 800/293; 800/298; 800/300.1; 800/320.1

(58) Field of Classification Search ................ 800/278, 800/293, 298, 300.1, 320.1
  See application file for complete search history.

(56) References Cited

FOREIGN PATENT DOCUMENTS

EP           0 586 355 A2    9/1994

OTHER PUBLICATIONS

Dunder E. et al. in Maize Transformation by Microprojectile Bombardment of Immature Embryos; Springer-Verlag, Berlin-Heidelberg; pp. 127-138.*
Altpeter et al., "Accelerated production of transgenic wheat (*Triticum aestivum* L.) plants", *Plant Cell Reports* 16:12-17 (1996).
Brettschneider et al., "Efficient transformation of scutellar tissue of immature maize embryos", *Theor. Appl. Genet.* 94:737-748 (1997).
Dunder et al., "Maize Transformation by Microprojectile Bombardment of Immature Embryos", Springer-Verlag Belin Heidelberg pp. 127-138 (1995).
Songstad et al., "Production of Transgenic Maize Plants and Progeny by Bombardment of HI-II Immature Embryos", *In Vitro Cell. Dev. Biol.—Plant* 32:179-183 (1996).
Takumi et al., "Production of Transgenic Wheat through Particle Bombardment of Scutellar Tissues: Frequency is Influenced by Culture Duration", *J. Plant Physiol.* 149:418-423 (1996).
Takumi et al., "Variation in transformation frequencies among six common wheat cultivars through particle bombardment of scutellar tissues", *Genes Genet. Syst.* 72:63-69 (1997).
Tomes et al., The effect of parental genotype on initiation of embryogenic callus from elite maize (*Zea mays* L.) germplasm, *Theor. Appl. Genet.* 70:505-509.
Tomes et al., Opportunities and limitations of the genotypic influences on establishment and plant regeneration from callus and cell cultures of crop species. In Biotechnology in Plant Science: Relevance to Agriculture in the Eighties, eds., P. Day, M Zilton and A. Hollaender; Academic Press, New York pp. 3-14 (1985).
Bohorova et al., "Production of transgenic tropical maize with *cryIAb* and *cryIAc* genes via microprojectile bombardment of immature embryos", *Theor. Appl. Genet.* 99:437-444 (1999).
Burkhardt et al., "Transgenic rice (*Oryza sativa*) endosperm expressing daffodil (*Narcissus pseudonarcissus*) phytoene synthase accumulates phytoene, a key intermediate of provitamin A biosynthesis", *The Plant Journal* 11(5):1071-1078 (1997).
Pastori et al., "Age-dependent transformation frequency in elite wheat varieties", *Journal of Experimental Botany* 52(357):857-863 (2001).
Rasco-Gaunt et al., "Procedures allowing the transformation of a range of European elite wheat (*Triticum aestivum* L.) varieties via particle bombardment" *Journal of Experimental Botany* 52(357):865-874 (2001).
Sivamani et al., "Resistance to wheat streak mosaic virus in transgenic wheat expressing the viral replicase (Nib) gene", *Molecular Breeding* 6:469-477 (2000).

* cited by examiner

*Primary Examiner*—Russell P. Kallis
(74) *Attorney, Agent, or Firm*—Pioneer Hi-Bred International, Inc.

(57) ABSTRACT

Methods are provided for transforming freshly isolated, immature maize embryos and for producing transgenic maize plants. The methods comprise obtaining immature embryos from a maize plant, contacting the embryos with an auxin-depleted or phytohormone-depleted transformation support medium and introducing a nucleotide construct into cells from the embryos prior to subjecting the embryos to conditions which promote embryogenic-tissue formation. The methods additionally comprise identifying or selecting transformed cells and regenerating such cells into transformed maize plants.

11 Claims, No Drawings

METHODS FOR TRANSFORMING IMMATURE MAIZE EMBRYOS

This application claims benefit of priority of U.S. Provisional Patent Application No. 60/248,427, filed Nov. 14, 2000, which is incorporated by reference herein.

FIELD OF THE INVENTION

The present invention relates to the field of genetic engineering. The invention further relates to transforming plant cells and regenerating transformed plants from transformed plant cells.

BACKGROUND OF THE INVENTION

The development of methods for the introduction of foreign genes into organisms has had a profound impact on fields of medicine and agriculture. While the movement of genes within plant species or between closely related plant species by traditional methods based on sexual reproduction has played an important role in crop improvement for most of this century, the pace of crop improvement by such methods has been slow and limiting due to the reliance on naturally occurring genes. Recent advances in the field of genetic engineering has led to the development of genetic transformation methods that allow the introduction of recombinant DNA, into organisms. The recombinant DNA methods which have been developed have greatly extended the sources from which genetic information can be obtained for crop improvement. Recently, new crop plant varieties, developed through recombinant DNA methods, have reached the marketplace. Genetically engineered soybeans, maize, canola and cotton are now widely utilized by North America farmers.

Rapid progress has been made in developing the tools for manipulating genetic information in plants. Plant genes are being cloned, genetic regulatory signals deciphered, and genes transferred from entirely unrelated organisms to confer new agriculturally useful traits to crop plants. Recombinant DNA methods significantly increase the gene pool available for crop improvement.

Maize or corn (*Zea mays*) is, on an economic basis, the most important crop grown in the United States. The continued success of American agricultural depends, to a large extent, on the continued success of U.S. maize producers. Certainly, a key factor that has lead to and helped maintain the preeminent position of maize in U.S. agriculture is the development of improved cultivars of maize. While maize geneticists and plant breeders have improved and will continue to improve maize through classical breeding approaches, molecular biologists have recently demonstrated that genetic engineering approaches may be employed to provide maize cultivars with new traits that were not attainable through classical breeding approaches. In only a few years since their initial release, commercial cultivars that have been genetically engineered for herbicide and insect resistance, have achieved phenomenal success.

While strides have been made in the genetic transformation of maize, a major difficulty in producing transgenic maize plants continues to be regenerating transformed maize cells into transformed maize plants. Thus, maize scientists have focused their efforts on transforming cells that have the greatest likelihood of being regenerated into a transformed plant. Maize scientists have utilized cells derived from maize embryos that have been subjected to culture conditions that are known to promote embryogenic-tissue formation. While such cells are amenable to transformation and regeneration, the recovery of transformed maize plants from a transformation attempt has been less than desirable. Methods employing cells from embryogenic-tissue cultures are both costly and laborious because such methods involve the development and maintenance of such cultures. Methods that involve the use of immature embryos themselves as the source of cells for transformation may be more desirable, particularly if the cells from the isolated embryos can be transformed soon after isolation. However, methods for transforming isolated, immature embryos have generally involved incubating the embryos after isolation for several days in culture under conditions which favor the formation of embryogenic tissue. Thus, improved methods for transforming maize cells and regenerating transformed maize plants are desired.

SUMMARY OF THE INVENTION

Methods are provided for transforming freshly isolated, immature maize embryos and for producing transgenic maize plants. The methods find use in the incorporation of new traits into cultivated maize plants. The methods comprise obtaining immature embryos from a maize plant and introducing a nucleotide construct into cells from the immature embryos prior to subjecting the embryos to conditions which promote embryogenic-tissue formation. The methods further comprise a transformation support medium that is auxin depleted or phytohormone depleted, and optionally comprise an osmoticum. The methods additionally comprise identifying or selecting transformed cells and regenerating such cells into transformed maize plants.

Also provided are methods that involve the introduction of a nucleotide construct into cells from an immature embryo by microprojectile bombardment. Such methods are particularly directed to the introduction of a nucleotide construct into cells of a freshly-isolated, immature embryo. Such methods comprise low-velocity delivery of the microprojectiles to the cells.

DETAILED DESCRIPTION OF THE INVENTION

The invention is drawn to methods for introducing nucleotide constructs into cells from maize plants and for producing stably transformed maize plants. The methods find use in developing new maize cultivars with improved agronomic characteristics. In particular, the methods involve introducing the nucleotide constructs into cells from freshly isolated, immature embryos. The invention provides methods that allow the introduction of the nucleotide construct into cells from such embryos on the same day that the immature embryos are isolated from the maize caryopsis. Thus, the methods of the invention provide improved methods of transforming cells from immature maize embryos that obviate the need for pre-culture and growth regulator(s) before the introduction of a nucleotide construct.

The present invention provides methods for transforming freshly isolated embryos which allow an individual to harvest a maize ear, isolate immature embryos and introduce a nucleotide construct into cells thereof in a single day. Such methods can reduce labor costs and also provide other cost savings by reducing the time and materials required for transforming immature maize embryos and regenerating transformed cells thereof into transformed plants.

A number of terms used herein are defined and clarified in the following section.

By "immature maize embryo" is intended a maize embryo that is physiologically less mature than the dormant embryo that would occur in a typical, viable, mature maize kernel.

By "freshly isolated, immature embryo" is intended a recently isolated embryo that is physiologically less mature than the dormant embryo that would occur in a w typical, viable, mature maize kernel. That is, the embryo has been dissected from the maize caryopsis fewer than about 12 hours before introducing a nucleotide construct into a cell thereof. Optionally, the embryo has been isolated fewer than 6 hours or fewer than 4 hours. Another option is that the embryo has been isolated fewer than 2 hours.

By "isolated embryo" is intended an embryo dissected from the maize caryopsis.

By "transformation support medium" is intended an auxin-depleted culture medium that an immature embryo is in contact with at the time a nucleotide construct is introduced into the embryo or cell thereof.

By "auxin depleted" is intended a culture medium that was prepared without the addition of any auxin or auxin-like growth regulator. A medium that is essentially auxin free or auxin depleted may contain other phytohormones or plant growth regulators.

By "phytohormone depleted" is intended a culture medium that was prepared without the addition of any phytohormone (also referred to as a plant growth regulator). A medium that is phytohormone depleted is auxin depleted.

By "effective amount" is intended an amount of an agent, compound or phytohormone that is capable of causing the desired effect on an organism. It is recognized that an "effective amount" may vary depending on factors, such as, for example, the organism, the target tissue of the organism, the method of administration, temperature, light, relative humidity and the like. Further, it is recognized that an "effective amount" of a particular agent may be determined by administering a range of amounts of the agent to an organism and then determining which amount or amounts cause the desired effect.

By "fresh embryo(s)" is intended embryo(s) placed directly onto a medium which conditions the tissue and cells for bombardment and does not effect an embryogenic response from the tissue either as a consequence of its composition or the period of time the embryo remains on the medium prior to bombardment.

By "pre-cultured embryo(s)" is intended embryo(s) cultured prior to bombardment on a medium which promotes the production of embryogenic tissue and precedes the conditioning of the embryo in preparation for particle bombardment. "Pre-cultured embryos" of maize are cultured for a period to produce an embryogenic response prior to particle bombardment. The tissue derived from the embryogenic response provides the target cells for transformation. Conditions during this period of pre-bombardment culture generally include a plant growth regulator and a period of time generally from one to seven days or more. The particular conditions depend on the culture medium formulation, genotype, and general health of the donor plant.

It is object of the present invention to provide improved methods for transforming freshly isolated, immature maize embryos. Particularly, the invention provides methods that do not depend on subjecting such embryos to conditions which are known to promote embryogenic-tissue formation prior to and/or during the introduction of a nucleotide construct. Generally, such conditions involve, inter alia, contacting an immature embryo with a culture medium containing an effective amount of an auxin. While the methods of the invention may involve the use of transformation support media containing phytohormones other than auxins, the methods of the present invention do not depend on the presence of any particular phytohormone in such media. In fact, embodiments of the present invention provide methods that involve the use of auxin-depleted transformation support media.

The present invention provides methods for transforming immature maize embryos. The methods of present invention do not depend on a pre-bombardment incubation to induce embryogenesis. An advantage of the present invention over existing methods is that the methods of the present invention eliminate the need to wait for embryogenic response before bombardment; freshly isolated immature embryos can be bombarded soon after isolation. This aspect of the present invention provides a particular advantage with maize genotypes that are known to exhibit a slow or poor in vitro embryogenic response.

Methods are provided for transforming freshly isolated, immature maize embryos and for producing transgenic maize plants. Such methods find use in the development of improved maize varieties as well as breeding lines which may be used to produce hybrid maize seeds. The methods involve obtaining immature embryos from a maize plant. The methods further involve contacting such an embryo with an auxin-depleted transformation support medium and introducing a nucleotide construct into at least one cell thereof. The methods for producing transgenic maize plants additionally involve regenerating such a transformed cell into a stably transformed maize plant.

One aspect of the invention is that the transformation support medium is a plant culture medium that is not known to promote embryogenic-tissue formation. One option is that such a transformation support medium is auxin depleted or phytohormone depleted. Alternatively, such a transformation support medium is an auxin-depleted or a phytohormone-depleted transformation support medium comprising a high concentration of an osmoticum or osmotic agent. The methods of the invention do not depend on a particular osmoticum. Any osmoticum known in the art may be employed in the methods of the invention. Osmoticum or osmotic agents of the invention include, but are not limited to, sucrose, maltose, sorbitol, mannitol, polyethylene glycol, glucose, fructose, other sugars, sugar alcohols and combinations thereof.

The methods of the invention can involve the use of a transformation support medium comprising a high concentration of an osmoticum. The osmoticum of the invention include compounds that are known to be metabolized by plants and compounds that are not known to be metabolized by plants. In fact, some of the osmoticum of the invention that are known to be metabolized by plants such as, for example, sucrose, glucose, fructose and maltose, are routinely used as a carbon source in plant culture media (Vain et al. (1993) *Plant Cell Rep.* 12:84–88) and immature maize embryos (Brettschneider et al. (1997) 94:737–748, Pareddy et al. (1997) *Maydica* 143–154; Dunder et al. (1995) In: Gene Transfer to Plants (Potrykus and Spangenberg, eds.) Springer-Verlag, NY, pp. 127–138).

By "high concentration" of such osmoticum is intended a concentration that is higher than that typically used when the osmoticum is intended solely as a carbon source. For example, sucrose is routinely used at a concentration of about 3% (w/v) as a carbon source in plant culture media. A high concentration of sucrose in a medium of the invention is a concentration that exceeds 3% (w/v). For other osmoticum of the invention, including those known to be metabolized by plants and those that are not known to be metabolized by plants, a "high concentration" is a concentration that generally exceeds the molar concentration of sucrose in a medium comprising 3% (w/v) sucrose. The osmoticum may be 8%, 12%, 19% or 30%w/v. Optionally, the osmoticum may be 12–19%.

The present invention encompass the use of both solid and liquid plant culture media. Those of ordinary skill in the art recognize that the preparation of solid plant culture media typically involves dissolving or suspending the various media components in a solution comprising water. It is recognized that the concentrations of components of such solid media referred herein are the concentrations of the components in the aqueous solution prior to solidification or gelling.

The present invention employs immature maize embryos. Such embryos are isolated from a maize ear that was pollinated preferably less than about 16 days before use, more preferably between about 6 and about 16 days before use, most preferably between about 9 and about 12 days before use. Generally, such embryos are between about 1.5 mm and 1.8 mm in length measured from the coleoptilar end to the coleorhizal end. Proper sizing of embryo for explant and transformation is best accomplished by developmental staging rather than by absolute size. Immature embryos are initially translucent. It is when the entire embryo, axis and scutellum, first become opaque, that they reach the proper developmental stage for use in the process. Immature embryos are cultured as soon after they become opaque as possible, but not before. Size of embryo (length) is roughly correlated with opacity, but both genotype and environment have dramatic altering effects on embryos size, and opacity is the preferred determinant.

Such ears may be obtained from field-, greenhouse- and growth-chamber-grown maize plants. Typically, the ear is harvested from the maize plant before isolation of the embryos therein, and is subsequently sterilized or otherwise treated to reduce undesired biological contamination, particularly microbial contamination. Methods are known in the art for reducing or eliminating microbial contamination from live plant tissues, such as maize ears, including, but not limited to, contacting the ear, preferably after removal of the husk, with an aqueous solution comprising household laundry bleach.

The methods of the invention involve the use of freshly isolated, immature embryos. In one method, the immature embryos are isolated from ears that were harvested in the same 24-hour period as the embryo isolation. However, the methods also encompass the use of ears that are stored for a period of time before embryo isolation. Any method of storing ears may be employed in the methods of the invention. It is recognized, however, that selected methods of ear storage conditions will substantially preserve the viability of the immature embryos therein. For the present invention, the age of an embryo is determined as the interval of time from pollination of the ear to isolation of the embryo therefrom. However, for an embryo that is isolated from an ear that was harvested on a day prior to the day of embryo isolation, the age of the embryo is the interval of time from pollination to harvest of the ear.

The freshly isolated, immature embryos of the invention may be obtained from a maize plant by any method known in the art. Typically, the embryos will be isolated from a de-husked ear by excising with a sharp-bladed instrument such as, for example, a scapel, knife or other sharp instrument. Upon isolation from an ear, the immature embryos are preferably contacted with transformation support medium. However, it is recognized that the immature embryos may be contacted with one or more alternative media before contacting the transformation support medium. It is further recognized that such alternative media are media that are not known to promote the formation of embryogenic maize callus and are preferably auxin-depleted or phytohormone-depleted media. Such alternative media may optionally comprise a high concentration of an osmoticum. Further it is recognized that "contacting" comprises both direct contact of an immature embryo with a medium and indirect contact such as, for example, an immature embryo placed on one side of a filter paper that has its opposite side in contact with the medium.

After contacting an isolated, immature embryo with transformation support medium, a nucleotide construct may be introduced into a cell of the embryo immediately thereafter or following a period of time, usually not more than about 24 hours after isolation of the immature embryo. Preferably, the nucleotide construct is introduced into a cell of the immature embryo within or less than about 12 hours after isolation of the embryo. More preferably, the nucleotide construct is introduced into a cell of the immature embryo within or less than about 6 hours after isolation of the embryo. Most preferably, the nucleotide construct is introduced into a cell of the immature embryo within or less than about 4 hours after isolation of the embryo. Another embodiment is the nucleotide construct is introduced into a cell of the immature embryo within or less than about 2 hours after isolation of the embryo.

The methods of the invention involve microprojectile bombardment to introduce nucleotide constructs into the cells of isolated, immature maize embryos. In particular, microprojectile bombardment may be conducted using a high pressure gas delivery system such as, for example, the invention described in U.S. Pat. No. 5,204,253, for which an embodiment known as Biolistic PDS-1000/He System is available commercially, or using any other device known in the art which is capable of delivering to a cell a nucleotide construct on or in microprojectiles.

In a second aspect, the present invention discloses methods comprising low-velocity delivery of a microprojectile coated with at least one nucleotide construct of interest. The invention discloses that such low-velocity delivery is one method for introducing a nucleotide construct into freshly isolated, immature maize embryos. By "low-velocity delivery" is intended that the microprojectile is traveling a relatively low velocity immediately prior to impacting a first plant cell and does not cause significant damage to the immature embryo. That is the velocity is less than that which would cause significant damage to the embryo. The level of damage to an embryo can be determined visually or by monitoring the biological response of the immature embryo for embryogenesis. Preferably, such low velocity delivery does not cause a significant reduction in the biological response of an immature embryo.

A variety of factors may control the velocity of a microprojectile immediately prior to impact with a first plant cell. For example, with the Biolistic PDS-1000/He System described supra, factors which may control the microprojectile velocity include, but are not limited to: microprojectile diameter; the psi (pounds per square inch) rating for the rupture disk which controls the release of pressurized helium that propels the macrocarrier in the direction of the target tissue; the distance between the macrocarrier starting platform and the rupture disk; the distance between the macrocarrier starting platform and the macrocarrier stopping screen; the distance between the macrocarrier stopping screen and the target cells; and the chamber pressure.

In one embodiment of the invention, the nucleotide construct is introduced into a cell of an immature maize embryo by low-velocity delivery of microprojectiles. Such low-velocity delivery of microprojectiles may be accomplished by, for example, using a high pressure gas delivery system including, but not limited to, the Biolistic PDS-1000/He System. Such low-velocity delivery with the PDS-1000 may employ a rupture disk with a psi rating of about 500 or less. Preferably, the rupture disk is selected from the group consisting of rupture disks with psi ratings of 100, 150, 200, 250, 300, 350, 400, 450 and 500. Additionally, the immature embryos may be placed in the chamber of the PDS-1000 in a position that allows the desired low-velocity delivery of microprojectiles. Preferably, the immature embryos are placed in the target platform in the chamber at a distance that is at least about 5 cm from the macrocarrier platform. More preferably, the immature embryos are placed in the chamber at a distance that is between about 5 cm and about 12 cm from the macrocarrier platform which is the starting position of the macrocarrier. Most preferably, the immature embryos are placed in the chamber at a distance that is between about 8 cm and about 12 cm from the macrocarrier platform. While the foregoing description pertains to the introduction of nucleotide constructs by microprojectile bombardment with the PDS-1000, the description is not intended to limit the invention in any way and is merely provided as an illustration of embodiments of the invention. Those of ordinary skill in the art will recognize, from such an illustration, that the low-velocity delivery of microprojectiles to immature embryos of the present invention may be achieved, in a like manner, with any microprojectile bombardment apparatus.

If desired, the immature embryo may be oriented on the transformation support medium for introduction of the nucleotide construct. For introduction by microprojectile bombardment, the immature embryos may be orientated to optimize entry of the nucleotide-construct-coated microprojectiles into a particular region of the immature embryo. Preferably, for microprojectile bombardment, the immature embryos are oriented with the scutellum of the immature embryos directly facing the expected path of the nucleotide-construct-coated microprojectiles. It is contemplated as part of this invention that the medium be solid, semi-solid or a solid surface floating on top of a liquid or semi-liquid surface (e.g. filter paper on liquid).

After the introduction of the nucleotide construct, the immature embryos may be transferred to an identification or selection medium, a regeneration medium or a medium that is for both identification/selection and regeneration. Such media comprise an auxin, particularly 2,4-D. Alternatively, an auxin can be added to a plate containing an auxin-depleted medium. The transfer to another medium or the addition of auxin to the medium may occur immediately following the introduction of the nucleotide construct or, if desired, after a period of time. Preferably, within about one week or less after the introduction of the nucleotide construct, the immature embryos are transferred from the transformation support medium to another medium, or auxin is added to the transformation support medium. More preferably, the embryos are transferred to another medium, or auxin is added to the transformation support medium, within about 2 to about 3 days after introduction of the nucleotide construct. Generally, the medium that the immature embryos are transferred to after introduction of the nucleotide construct will depend on the method by which the nucleotide construct was introduced into cells of the immature embryos, the nucleotide construct and the desired outcome. The medium used may additionally comprise other components such as, for example, antibiotics.

The transformed cells may be identified or selected and, if desired, regenerated into transformed plants. The methods of the invention do not depend on any particular method for identifying or selecting transformed cells from immature embryos and for regenerating such cells into transformed maize plants. Identification methods may involve utilizing a marker gene, such as GFP, or a cell cycle gene, such as CKI, Cyclin D. Methods for using GFP and cell cycle genes are found in U.S. Pat. Nos. 6,300,543, 60/246,349 and 09/398,858 and are incorporated by reference. Selection methods typically involve placing the immature embryos, or parts thereof, on a medium that contains a selective agent, promotes regeneration or both. If, for example, the nucleotide construct comprises a selectable marker gene for herbicide resistance that is operably linked to a promoter that drives expression in a plant cell, then selection of the transformed cells may be achieved by adding an effective amount of the herbicide to the medium to inhibit the growth of or kill non-transformed cells. Such selectable marker genes and methods of use are well known in the art. Methods and media employed in the regeneration of transformed maize plants from transformed cells of immature embryos are also known in the art. Generally, such methods comprise contacting the immature embryo with a medium that contains an effective amount of an auxin. Any method known in the art for identifying or selecting transformed plant cells and regenerating transformed maize plants may be employed in the methods of the present invention.

The methods of the invention do not depend on a particular nucleotide construct. Any nucleotide construct that may be introduced into a plant cell may be employed in the methods of the invention. Nucleotide constructs of the invention comprise at least one nucleotide sequence of interest operably linked to a promoter that drives expression in a plant cell. The nucleotide constructs may also comprise identification or selectable marker gene constructs in addition to the nucleotide sequence of interest.

Selectable marker genes may be utilized for the selection of transformed cells or tissues. Selectable marker genes include genes encoding antibiotic resistance, such as nptII which encodes neomycin phosphotransferase II (NEO), hpt which encodes hygromycin phosphotransferase (HPT), and the moncot-optimized cyanamide hydratase gene (moCAH) (see U.S. Pat. No. 6,096,947) as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp.177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:46474653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology, Vol.* 78 (Springer-Verlag, Berlin); Gill et al. (1988) *Nature* 334: 721–724. Such disclosures are herein incorporated by reference.

The above list of selectable marker genes is not meant to be limiting. Any selectable marker gene can be used in the present invention. Other marker genes such as GFP (WO97/41228) may also be utilized.

Likewise, the methods of the invention do not depend on immature maize embryos of a particular genotype. The methods of the present invention may be used with immature maize embryos of any maize genotype including immature embryos from both hybrids and inbreds. Examples of maize genotypes include, but are not limited to, Hi-II and hybrids of a cross between Hi-II and a second genotype such as, for example, PHN46, PHTE4, PHAA0, PHP18, PH05F, PH09B, PHP02, PHJ90, PH24E, PHT05, ASKC27 and PH21T. However, it is recognized in the art that the transformation of cells from immature embryos and particularly, the regeneration of such cells into transformed maize plants varies from one genotype to another. While the methods of the invention disclosed herein may be used with any genotype, it is recognized that certain embodiments may be used for a first genotype and other embodiments may be used for a second genotype.

Methods of the invention involve producing a stably transformed maize plant. Such a transformed maize plant is a maize plant that is capable of producing at least one progeny. Preferably, such a transformed maize plant is capable of producing at least one transformed progeny.

The methods of the invention involve the use of plant culture media. Any plant culture medium known in the art may be employed in the methods of the invention including, but not limited to, a transformation support medium, an identification or selection medium and a regeneration medium. Typically, such media comprise water, a basal salt mixture and a carbon source, and may additionally comprise one or more other components known in the art, including but not limited to, vitamins, co-factors, myo-inositol, selection agents, charcoal, amino acids, silver nitrate and phytohormones. If a solid plant culture medium is desired, then the medium additionally comprises a gelling agent such as, for example, gelrite, agar or agarose.

For example, transformation support medium 560Y comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium 560R comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium 288J comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Phytohormone-depleted medium 272V comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

The methods of the present invention can involve the use of phytohormones or plant growth regulators such as, for example, auxins, cytokinins, gibberellins and ethylene. The phytohormones of the invention include, but are not limited to, both free and conjugated forms of naturally occurring phytohormones or plant growth regulators. Additionally, the phytohormones of the invention encompass synthetic analogues and precursors of such naturally occurring phytohormones and synthetic plant growth regulators.

Naturally occurring and synthetic analogues of auxins and auxin-like growth regulators include, but are not limited to, indoleacetic acid (IAA), 3-indolebutyric acid (IBA), a-napthaleneacetic acid (NAA), 2,4-dichlorophenoxyacetic acid (2,4-D), 4-(2,4-dichlorophenoxy) butyric acid, 2,4,5-trichlorophenoxyacetic acid (2,4,5-T), 3-amino- 2,5-dichlorobenzoic acid (chloramben), (4-chloro-2-methylphenoxy) acetic acid (MCPA), 4-(4-chloro-2-methylphenoxy) butanoic acid (MCPB), mecoprop, dicloprop, quinclorac, picloram, triclopyr, clopyralid, fluroxypyr, dicamba and combinations thereof. It is recognized that such combinations can be comprised of any possible combination of two or more molecules selected from the group consisting of naturally occurring auxins synthetic analogues of auxins and auxin-like growth regulators. By "auxin-like growth regulator" is intended a compound that is not considered an auxin but possesses at least one biological activity that is the substantially the same as that of a naturally occurring auxin.

Examples of phytohormones include naturally occurring, synthetic analogues of cytokinins and cytokinin-like growth regulators include, but are not limited to, kinetin, zeatin, zeatin riboside, zeatin riboside phosphate, dihydrozeatin, isopentyl adenine 6-benzyladenine and combinations thereof. It is recognized that such combinations can be comprised of any possible combination of two or more molecules selected from the group consisting naturally occurring cytokinins, synthetic analogues of cytokinins and cytokinin-like growth regulators. By "cytokinin-like growth regulator" is intended a compound that is not considered a cytokinin but possesses at least one biological activity that is the substantially the same as that of a naturally occurring cytokinin.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs which can be employed in the methods of the present invention for transforming maize plants including, but not limited to, those comprised of deoxyribonucleotides, ribonucleotides and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures and the like.

Furthermore, it is recognized that the methods of the invention may employ a nucleotide construct that is capable of directing, in a transformed plant, the expression of at least one protein, or at least one RNA, such as, for example, an rRNA, a tRNA and an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the genome of the maize plant is altered as a result of the introduction of the nucleotide construct into a maize cell. Alterations to the genome include additions, deletions and substitution of nucleotides in the genome. While the methods of the present invention do not depend on additions, deletions, or substitutions of any particular number of nucleotides, it is recognized that such additions, deletions or substitutions comprise at least one nucleotide.

The nucleotide constructs of the invention also encompass nucleotide constructs, that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821 and Beetham et al. (1999) *Proc. Natl. Acad. Sci. USA* 96:8774–8778; herein incorporated by reference.

The nucleotide constructs of the invention may be comprised of expression cassettes for expression in the maize plant of interest. The expression cassette will include 5' and 3' regulatory sequences operably linked to a gene of interest sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the gene of interest sequence to be under the transcriptional regulation of the regulatory regions. The expression cassette may additionally contain identification or selectable marker genes.

The expression cassette will include in the 5'-3' direction of transcription, a transcriptional and translational initiation region, a gene of interest sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the gene of interest using heterologous promoters, the native promoter sequences may be used. Such constructs would change expression levels of the gene of the interest in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391 and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5'-leader sequences in the expression cassette construct. Such leader sequences can act to enhance translation. Translation leaders are known in the art and include: picornavirus leaders, for example, EMCV leader (Encephalomyocarditis 5'-noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in maize plants.

Such constitutive promoters include, for example; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026); SCP (WO 97/47756A1, WO 99/438380) and the like. Other constitutive promoters include, for example, U.S. Pat. Nos. 5,608,149; 5,608,144; 5,604,121; 5,569,597; 5,466,785; 5,399,680; 5,268,463; and 5,608,142.

Tissue-preferred promoters can be utilized to target enhanced expression of the gene of interest within a particular plant tissue. Tissue-preferred promoters include Yamamoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see the copending application entitled "Seed-Preferred Promoters," WO00/11177, herein incorporated by reference). For dicots, seed-specific promoters include, but are not limited to, bean β-phaseolin, napin, β-conglycinin, soybean lectin, cruciferin, and the like.

Depending on the desired result, it may be beneficial to express a gene under the control of an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also the copending application entitled "Inducible Maize Promoters," WO99/43819, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes or nucleotide sequences of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increases, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Grain traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. No. 5,990,389 issued Nov. 23, 1999, U.S. Pat. No. 5,885,801 issued Mar. 23, 1999, U.S. Pat. No. 5,885,802 issued Mar. 23,1999 and U.S. Pat. No. 5,703,409; herein incorporated by reference. Another example is lysine and/or sulfur rich seed protein encoded by the soybean 2S albumin described in U.S. Pat. No. 5,850, 016 issued Dec. 15, 1998, and the chymotrypsin inhibitor from barley, Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor WO98/20133 and WO98/20133 which are incorporated herein by reference. Other proteins include methionine-rich plant proteins such as from corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiseretal. (1986) *Gene* 48:109); lectins (Van Damme et al. (1994) *Plant Mol. Biol.* 24:825); and the like.

Genes encoding disease resistance traits include detoxification genes, such as against fumonosin (U.S. application Ser. No. 08/484,815, filed Jun. 7, 1995); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical emasculation. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of seed is reflected in traits such as levels and types of oils, saturated and unsaturated, quality and quantity of essential amino acids, and levels of cellulose. For example, U.S. Pat. Nos. 5,990,389; 5,885,801; and 5,885, 802 and 5,703,409, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutryrate synthase), and acetoacetyl-CoA reductase (see Schubert et al. (1988) *J. Bacteiol.* 170:5837–5847) facilitate expression of polyhydroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

It is recognized that a nucleotide construct of the present invention may comprise an antisense construction complementary to at least a portion of a messenger RNA (mRNA) of a gene of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the complementary sequences may be used. Furthermore, portions of the antisense nucleotides may be used to disrupt the expression of the target gene. Generally, sequences of at least 50 nucleotides, 100 nucleotides, 200 nucleotides, or greater may be used. Typically, such antisense constructions will be operably linked to a promoter that drives expression in a plant.

The nucleotide constructs of the invention may also be employed in sense suppression methods to suppress the expression of endogenous genes in plants. Methods for suppressing gene expression in plants using nucleotide sequences in the sense orientation are known in the art. The methods generally involve transforming plants with a nucleotide construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The following examples are presented by way of illustration, not by way of limitation.

EXPERIMENTAL

EXAMPLE 1

Particle Gun Terminology and Use

The PDS-1000 Biolistics particle bombardment device is schematically shown in FIG. 1. The operation of this device is detailed in the operating instructions available from the manufacturer (Bio-Rad Laboratories, Hercules, Calif.).

Briefly, DNA and particles of materials with large specific gravity (i.e. W, Au, Pd, Pt) are associated and the preparation is dried on plastic macrocarriers. Such particles are also known as microparticles or microprojectiles. Prior to each bombardment, the expendables are mounted in the device. Expendables include the macrocarrier with a dried DNA/particle preparation, a rupture disk, and a stopping screen. The material intended to be bombarded is positioned upon on target platform.

Next, the chamber of the device is evacuated with a vacuum pump to near 28 mm Hg. A small reservoir behind the rupture disk is then slowly filled with He. When the He pressure in this chamber rises sufficiently, the rupture disk breaks and releases a burst of He. The He burst pushes against the macrocarrier and accelerates it towards the stopping screen. The stopping screen, a metal mesh, abruptly stops the macrocarrier. The DNA/particles preparation that is dried upon the macrocarrier are released from the macrocarrier and continue on a path to strike the target. The chamber is equalized with the atmosphere, and the expendibles are removed.

Variables in the use of the device include the psi at which the rupture dish breaks, the composition and size of particles, position of the target shelf, and vacuum in the chamber during bombardment.

The macrocarrier flight distance is fixed in the instrument at ¼" (0.25"). While the rupture disk-macrocarrier gap distance is adjustable, the device was operated at the factory recommended distance of ⅛" (0.125").

EXAMPLE 2

Association of Particles with Transforming DNA

The transforming DNA was associated with either tungsten or gold particles. Prior to association with the transforming DNA, the tungsten particles were prepared essentially as described by Tomes et al. (U.S. Pat. No. 5,990,387). Gold particles were prepared as follows. Sixty mg of 0.6 µ gold particles (Bio-Rad) were placed in 2.0 mL Sarstedt tube. The particles were washed three times in absolute ethanol (100%). Each ethanol wash involved adding one mL of absolute ethanol to the tube, sonicating the tube briefly, vortexing the tube on high for one minute, centrifuging the tube to pellet the particles and discarding the supernatant. The particles were then washed two times in sterile deionized water. Each wash involved adding one mL of sterile deionized water to the tube, sonicating the tube briefly, vortexing the tube on high for one minute, centrifuging the tube to pellet the particles and discarding the supernatant. Following the ethanol and water wash steps, one mL of sterile deionized water was added to the tube and the tube was sonicated. Aliquots (250 µL) of the particle-containing suspension were removed to siliconized 1.5 mL tubes and combined with 750 µL sterile deionized water. The 1.5 mL tubes were frozen until later use.

The transforming DNA was associated with the prepared tungsten or gold particles by precipitation in a solution comprising $CaCl_2$ and spermidine as follows. A tube containing tungsten or gold particles prepared as described above, was thawed, if frozen, and sonicated for 3 seconds at setting 2.5 in a water bath probe, Branson Sonicator #450 (Branson Ultrasonics Corp., Danbury Conn.). Ten µL plasmid DNA (1 µg plasmid total) in TE buffer was added to the tube and mixed for 5 seconds. Next, 100 µL 2.5 M $CaCl_2$ and 10 µL 0.1 M spermidine were added. The tube was then shaken on a vortexer for 10 minutes followed by centrifugation for 30 seconds at 10,000 rpm. The supernatant was removed and discarded, and 500 µL absolute ethanol was added. The tube was then sonicated at setting 2.5 for 3 seconds, centrifuged for 30 seconds at 10,000 rpm and the supernatant removed. To the tube, 105 µL of absolute ethanol was added. The tube was sonicated for 3 seconds at setting 2.5 before placing a 10 µL aliquot onto the center of a macrocarrier.

EXAMPLE 3

Transient Delivery of DNA to Fresh Embryos to Ascertain Preferred Particle Type and Composition, Rupture Disk, and Distance From Macrocarrier Transient gene expression assays were performed to quickly identify limits to the values of certain transformation parameters. These limits were then used to define parameter limits and experimental design for stable transformation assays. Transient assays indicated that DNA was delivered to cells in the target tissue, and that the recipient cells lived long enough to process the DNA, produce RNA, and synthesize the protein encoded by the transferred gene. In the transient assays used for these experiments, the reporter gene GUS (uidA) was used in conjunction with a fluorometric assay for GUS enzymatic activity. The greatest transient expression therefore, generally reports the most effective treatment for DNA delivery—a function of cells successfully targeted and the number of DNA templates delivered per cell.

Additional assays were conducted to evaluate embryogenic responsiveness subsequent to particle bombardment. Transformation target cells are contained within the scutellum of the immature embryo. The goal of particle bombardment is to deliver DNA to these target cells. The target cells may be several cell diameters removed from the scutellum surface. Certain levels of bombardment parameters, while providing for effective DNA delivery to target cells, nevertheless can cause such damage to the scutellum that an effective embryogenic response, sufficient to support the establishment, emergence and growth of transgenic events, is precluded. For efficient stable transformation, it is undesirable for bombardment procedures to significantly reduce embryogenic responsiveness.

One embodiment of DNA delivery parameters include those conditions that provide for the greatest DNA delivery, as assayed by GUS specific activity, but promote the least damage to immature embryos as determined by normal, or near normal embryogenic responsiveness.

Preparation of Target Tissue

Ears of genotype Hi-II were sampled in planta to assess the developmental stage of the embryos. When immature embryos first became opaque, about 9–12 days post-pollination, the ears were harvested for embryo dissection. The embryos were approximately 1.5–1.8 mm long from coleoptilar to coleorhizal end. Immature embryos were the target tissue for transient and stable transformation experiments.

The ears were surface sterilized in 50% (v/v) Clorox bleach+0.5% (v/v) Micro detergent for 20 minutes, and then rinsed twice with sterile water. The immature embryos were excised from the caryopsis and placed embryo axis side down (scutellum side up) onto transformation support medium.

For fresh embryo bombardments, the embryos were cultured on 560Y medium without 2,4-D in darkness at 28° C. for four hours prior to bombardment. The embryos were cultured and bombarded scutellum surface upward. Ten embryos per target plate were arranged in a 2 cm target zone.

DNA/Particle Association

Particles of 0.6μ 1μ Au and 1μ W were prepared and associated with plasmid DNA as in Example 2; CaMV35S-1841:Ω':adh1$_{int}$::BAR::pinII/ubi:ubi$_{int}$::GUS::pinII.

Bombardment of Fresh Immature Embryos

The PDS-1000 Particle Gun was used as described in Example 1.

Target plates were bombarded at target platform positions 1, 2, or 3 and at rupture disk pressures of 200, 650, and 1100 psi. All plates were bombarded once at a chamber vacuum of 28 mmHg. A repetition of each experiment consisted of the embryos from a single ear being distributed across all the treatments. The experiment was repeated five times with embryos from different ears. After bombardment, 2,4-D was added to the plates from sterile concentrated stocks to a final concentration of 2 ppm, and the plates were incubated in darkness at 28° C. for two days.

For analysis, immature embryos were sampled, by treatment and by ear, for the GUS fluorometric assay using MUG (4-Methylumbelliferyl beta-D-glucuronide) (SPOERLEIN-B; MAYER-A; DAHLFELD-G; KOOP-H-U (1991) A microassay for quantitative determination of beta-glucuronidase reporter gene activities in individually selected single higher plant cells. PLANT SCIENCE 78:73–80). GUS specific activity was expressed as μmols MUG/mg protein/hr. Three repetitions per treatment were conducted, and GUS assays were executed on six embryos/treatment/replication. The mean expression per treatment was averaged across the repetitions. Subsequently, relative GUS expression was computed by dividing the mean specific activity per treatment by the largest treatment specific activity.

Culture growth assays for embryogenic responsiveness were conducted as analysis for GUS specific activity except that after the two-day post-bombardment incubation, the embryos were transferred to 560 L medium. After two weeks incubation in darkness at 28° C., the embryos were scored for embryogenic responsiveness. Embryogenic responsiveness was calculated as the number of embryos that produced a friable embryogenic tissue culture in a treatment (type II-embryogenic response) divided by the total number of embryos handled in the treatment. Maximal response was 95–100%, which was typical for unbombarded Hi-II embryos.

Results

Transient assays using the GUS reporter gene indicated that 650 psi was the generally preferred rupture disk for maximal DNA delivery, pooled across shelf levels and particle types (Table 1). Six-tenths micron gold particles was the preferred delivery vehicle, pooled across shelf levels and rupture disk psi. Shelf 3, the closest to the stopping screen, was preferred for maximal transient expression, pooled across particle types and rupture disk psi. Specifically, 0.61μ Au, 650 psi, and shelf 3 was the preferred combination of treatment levels to effect maximal DNA delivery (Table 1).

TABLE 1

Transient Gene Expression Assay to Ascertain Optimal Particle Type, Shelf, and PSI

| | | Relative GUS Expression Shelf | | |
|---|---|---|---|---|
| | PSI | 1 | 2 | 3 |
| 0.6 μAu | 200 | 0.27 | 0.39 | 0.59 |
| | 650 | 0.31 | 0.49 | 1.00 |
| | 1100 | 0.72 | 0.66 | 0.64 |
| 1 μAu | 200 | 0.08 | 0.24 | 0.54 |
| | 650 | 0.23 | 0.32 | 0.46 |
| | 1100 | 0.24 | 0.21 | 0.28 |
| 1 μW | 200 | 0.14 | 0.26 | 0.59 |
| | 650 | 0.25 | 0.35 | 0.40 |
| | 1100 | 0.25 | 0.30 | 0.37 |

Culture growth assays indicated that 200 psi was the generally preferred rupture disk for maximal embryogenic responsiveness, pooled across particle types and shelf levels (Table 2). Six-tenths micron gold particles and 1μ W were the preferred particle types, pooled across shelf levels and rupture disk psi. Shelf 1, the furthest from the stopping screen, was preferred for maximal embryogenic responsiveness, pooled across particle types and rupture disk psi. Specifically, 1μ W, 200 psi, and shelf 1 was the preferred combination of treatment levels to effect maximal embryogenic responsiveness (Table 2).

The overall preferred combination projected to effect the highest frequency of stable transformation in freshly excised immature embryos, based on transient DNA delivery assays, and culture growth assays, was 0.6μ Au or 1μ W, 200 psi, and shelf 1 or shelf 2.

TABLE 2

Embryogenic Responsiveness Assay to Ascertain Optimal Particle Type, Shelf, and PSI

| Particle | PSI | Frequency of Embryogenic Responsiveness Shelf | | |
|---|---|---|---|---|
| | | 1 | 2 | 3 |
| 0.6 µAu | 200 | 0.86 | 0.61 | 0.11 |
| | 650 | 0.82 | 0.39 | 0.14 |
| | 1100 | 0.57 | 0.36 | 0.07 |
| 1 µAu | 200 | 0.75 | 0.46 | 0.07 |
| | 650 | 0.71 | 0.25 | 0.14 |
| | 1100 | 0.71 | 0.29 | 0.04 |
| 1 µW | 200 | 0.93 | 0.64 | 0.07 |
| | 650 | 0.86 | 0.57 | 0.25 |
| | 1100 | 0.57 | 0.43 | 0.07 |

EXAMPLE 4

Transformation of Freshly Excised Immature Embryos with and Without Prior 2,4-D Exposure Methods Fresh embryos were prepared as in Example 3, except, in a paired comparison, half the embryos from an ear were cultured on 560Y without 2,4-D, while the remaining embryos were pre-cultured on 560Y with 2 ppm 2,4-D. The level of 2,4-D used in the latter formulation is a concentration widely used in the art to effect an embryogenic response from maize immature embryos.

After a four-hour incubation at 28° C. in darkness, the embryos were bombarded with 1µ W particles associated with plasmid DNA as in Example 3. This DNA plasmid contains a GUS reporter gene and a selectable marker gene which confers resistance to the herbicide bialaphos. Target plates were bombarded on shelf 1, at 200 psi. After bombardment, 2,4-D was added to those plates lacking 2,4-D. The bombarded plates were incubated in darkness at 28° C. for two days. After the two-day bombardment recovery period, the embryos were transferred to Petri dishes containing 560R medium. This latter medium is comprised of those components which typically are used to initiate and promote embryogenic tissue from maize embryos, and contains 2% sucrose, and 3 ppm bialaphos as a selective agent. The plates were incubated in darkness at 28° C. for 4–6 weeks, or until growth of putatively transformed events were observed. 560R culture medium does not support the growth of untransformed tissue derived from the bombarded embryos. Therefore, only putatively transformed tissue, resistant to bialaphos as a consequence of expressing the resistance transgene, are competent to grow.

Putatively transformed events were identified first by their growth under selective conditions and individually subcultured to fresh 560R medium for propagation. Samples of each event were assayed for their transgenic nature by immersing pieces of the embryogenic tissue ("frequently termed embryogenic callus" or "callus", although embryogenic tissue is not callus in the botanical meaning) into 5 volumes of McCabes histochemical reagent. Those putative events that stained blue were considered to be confirmed transgenic events. Transformation frequency was computed by dividing the number of transgenic events derived from a population of embryos used in a treatment divided by the total number of embryos used in the treatment.

Results

Transgenic events were produced from embryos derived from five different ears. Based on GUS histochemical staining reaction, the transformation frequency effected by the two treatments was about the same (Table 3). Therefore, maize immature embryos do not require embryogenic induction by 2,4-D or other auxin-like growth regulator prior to bombardment to effect stable transformation.

TABLE 3

Effect of 2,4-D on Transformation Frequency

| Treatment | Transformation Frequency |
|---|---|
| No 2,4-D in pre-bombardment phase | 4.1% |
| 2-4-D present in pre-bombardment phase | 3% |

EXAMPLE 5

Transformation of Freshly Excised Immature Embryos Relative to Pre-Cultured Embryo Methods Fresh embryos were prepared for bombardment as in Example 3 and Example 4, with no 2,4-D present during the four-hour, pre-bombardment conditioning period. Plasmid DNA and 1µ W particles were associated as in Example 2 and 3.

For cultured embryo bombardments, embryos from the same ears used for fresh embryo bombardments were pre-cultured on 560L medium for 4–5 days in darkness at 28° C. At this time, a small amount of incipient embryogenic tissue can be observed at the coleorhizal end of the scutellum. As preparation for bombardment, the embryos were transferred to 560Y and incubated in darkness at 28° C. for 4 hours. The embryos were arranged, 10 embryos per plate, in a 2 cm target zone. The embryos were angled with their coleorhizal end pointing up toward the macrocarrier at approximately a 300 angle. This orientation of the pre-cultured embryos enhances exposure of the preferred cell targets to the path of particles propelled by the particle gun.

Plates of pre-cultured embryos were bombarded at shelf 2, while fresh embryos were bombarded on shelf 1 as identified in Example 3. Plates were bombarded at different rupture disk psi, with a chamber vacuum of 28 mm Hg.

After bombardment, the embryos were handled as in Example 4 for the production of transgenic events.

Results

Transgenic events were produced from fresh immature embryos not exposed to 2,4-D and from embryos pre-cultured prior to bombardment on medium containing 2,4-D (Table 4). Fresh embryos required a significantly reduced rupture disk psi to achieve the same transformation frequency relative to pre-cultured embryos. Since the fresh embryos were not exposed to 2,4-D prior to bombardment, auxin-induced embryogenic induction is not required as a prerequisite to stable transformation in maize embryos.

TABLE 4

Frequency of Transgenic Event Production from Fresh vs Pre-cultured Immature Embryos

| | Transformation Frequency | |
|---|---|---|
| Rupture Disk (psi) | Freshly Excised Immature Embryos | Pre-cultured Immature Embryos |
| 200 | 15.1 | 6.3 |
| 400 | 8.1 | 11.1 |
| 650 | 3.2 | 15.3 |
| 1100 | 0 | 12 |
| 1500 | 0 | 0 |

EXAMPLE 6

Stable Transformation of Freshly Excised Embryos Without 2,4-D Induction

Effect of Shelf Level

Example 3 taught that the preferred combination of bombardment parameters to effect the highest frequency of stable transformation in freshly excised immature embryos, based on transient DNA delivery assays, and culture growth assays, was 0.6μ Au or 1μ W, 200 psi, and shelf 1 or shelf 2. Stable transformation assays were performed, therefore, to more precisely identify the preferred shelf level conditions to produce transgenic events with maximal frequency.

Methods

Fresh embryos were prepared as in Example 3. Plasmid DNA was associated with 0.6μ and 1μ W particles as in Example 2.

Target plates of embryos were bombarded in a paired comparison, grouped by ear. Particles were delivered at 200 psi, and the plates were bombarded on shelf 1 or shelf 2, at a chamber vacuum of 28 mmHg.

Bombarded plates were handled as in Example 4 for the production of transgenic events. Events were scored as in Example 4.

Results

There was no statistical difference between shelf 1 and shelf 2 for 1μ W particles. In contrast, transformation frequency was significantly enhanced at shelf 2 relative to shelf 1 with 0.6μ Au particles (Table 5). Although the experiments were not conducted as comparison pairs to evaluate the effect of particle type on transformation frequency, qualitatively, 0.6μ Au performed better than 1μ W. Sixteen ears were used for the Au comparison, while 5 ears were used for the W comparison.

TABLE 5

Effect of Shelf Level on Stable Transformation of Fresh Hi-II Immature Embryos using Two Particle Types
Transformation Frequency

| | Shelf | | |
|---|---|---|---|
| Particle Prep. | 1 | 2 | $\chi^2$ |
| 0.6 μ Au/CaCl$_2$-spermidine | 13% | 17% | 4.8* |
| 1 μW/CaCl$_2$-spermidine | 2% | 3% | 0.56 ns |

[*= P < 0.05; ns = not statistically significant]

EXAMPLE 7

Stable Transformation of Freshly Excised Embryos Without 2,4-D Induction: Effect of Particle Size and Composition Example 3 taught that the preferred combination of bombardment parameters to effect the highest frequency of stable transformation in freshly excised immature embryos, based on transient DNA delivery assays, and culture growth assays, was 0.6μ Au or 1μ W, 200 psi, and shelf 1 or shelf 2. Example 6 taught that shelf 2 was the preferred level to maximize stable transformation. Stable transformation assays were performed, therefore, to more precisely identify the preferred particle type necessary to produce transgenic events with maximal frequency.

Methods

Fresh embryos were prepared as in Example 3. Plasmid DNA was associated with 0.6μ and 1μ W particles prepared as described in Example 2.

Target plates of embryos were bombarded in a paired comparison, grouped by ear. Particles were delivered at 200 psi, and the plates were bombarded on shelf 2, under a chamber vacuum of 28 mmHg. Seven ears were processed for the completed experiment.

Bombarded plates were handled as in Example 4 for the production of transgenic events.

Results

By a large measure, 0.6μ Au particles were preferred to 1μ W (Table 6).

TABLE 6

Effect of Particle Type on Stable Transformation of Fresh, non-Embryogenically Induced Hi-II Immature Embryos

| Particle Type | Transformation Frequency |
|---|---|
| 1 μW | 4% |
| 0.6 μAu | 21% |
| | $\chi^2$ = 48.7** |

[**= P < 0.01]

EXAMPLE 8

Transient and Stable Transformation of Freshly Excised Embryos Without 2,4-D Induction: Effect of Osmotic Agent Example 3 taught that the preferred combination of bombardment parameters to effect the highest frequency of stable transformation in freshly excised immature embryos, based on transient DNA delivery assays, and culture growth assays, was 0.6μ Au or 1μ W, 200 psi, and shelf 1 or shelf 2. Example 6 taught that shelf 2 was the preferred level to maximize stable transformation. Example 7 taught that 0.6μ Au was the preferred particle type to maximize stable transformation.

An osmotic conditioning agent or osmoticum is beneficial to particle gun mediated transformation. While the precise mechanism has not been identified, a preferred explanation holds that plasmolyzed cells, a consequence of an osmotic conditioning treatment, are less apt to lyse when penetrated by a particle.

While osmotic pre- and post-treatment is beneficial, some osmotically active agents may be toxic to subsequent growth and differentiation of targeted cells. To recover events from bombarded maize embryos, the type and concentration of osmotic agent or osmoticum must not be deleterious to embryogenic responsiveness. In maize, sucrose, at 12% (w/v) has been used effectively as an osmotic agent prior to bombardment of embryogenic tissue and cultured immature embryos. The proper sucrose concentration to osmotically treat for fresh, non-2,4-D treated embryos prior to bombardment may be different than that used for embryos pre-cultured prior to bombardment.

Experiment #1 Effect of Osmotic Agent on Embryogenic Responsiveness

Methods

Fresh embryos were prepared as in Example 3 except the embryos were cultured on 560Y without 2,4-D medium modified to contain 2, 8, 12, 19, or 30% (w/v) sucrose. Embryos from a individual ears were distributed across all media formulations. Plasmid DNA was associated with 0.6μ Au particles as in Example 2.

Target plates of embryos were bombarded, as in Example 3, in a paired comparison, grouped by ear. Particles were delivered at 200 psi to plates on shelf 1, under a chamber vacuum of 28 mmHg.

Transient gene expression assay was conducted as in Example 3. Assays for embryogenic responsiveness were conducted as in Example 3.

Results

The concentration of sucrose had no effect on embryogenic responsiveness (Table 7). Therefore, no relevant damage occurred to the embryos as a consequence of sucrose conditioning and bombardment.

TABLE 7

Effect of Sucrose Concentration on Embryogenic Responsiveness of Hi-II Immature Embryos

| Sucrose Concentration in Bombardment Medium (%) | % Immature Embryos that Produce Embryogenic Tissue |
| --- | --- |
| 2 | 100 |
| 8 | 100 |
| 12 | 100 |
| 19 | 94 |
| 30 | 100 |
| 2, no bombardment control | 100 |

Transient expression of GUS was optimal when fresh embryos were conditioned with 12–19% sucrose prior to bombardment (Table 8).

TABLE 8

Transient Expression of the GUS Reporter Gene after Delivery to Immature Embryos Conditioned with Various Concentrations of Sucrose

| Sucrose Concentration in Bombardment Medium (%) | Relative Transient GUS Expression |
| --- | --- |
| 2 | 0.39 |
| 8 | 0.65 |
| 12 | 1 |
| 19 | 0.76 |
| 30 | 0.67 |
| 2, no bombardment control | 0.003 |

Experiment #2

Methods

Fresh embryos were prepared as in Example 3 except they were cultured on 560Y medium without 2,4-D but modified to contain 12% or 19% sucrose. Embryos from nineteen individual ears were distributed across both media formulations. Plasmid DNA was associated with 0.6μ Au particles as in Example 2.

Target plates of embryos were bombarded, as in Example 3, in a paired comparison, grouped by ear. Particles were delivered at 200 psi to plates on shelf 1, under a chamber vacuum of 28 mmHg.

Bombarded plates were handled as in Example 4 for the production of transgenic events.

Results

Stable transformation assays revealed that 19% sucrose was the preferred sucrose concentration pre- and post-bombardment to effect optimal transformation frequency with fresh, non-2,4-D-induced, embryos (Table 9).

TABLE 9

Effect of Sucrose Concentration on Stable Transformation of Fresh, non-Embryogenically Induced Hi-II Immature Embryos

| % Sucrose (w/v) | Average Transformation Frequency |
| --- | --- |
| 12% | 14% |
| 19% | 24% |
| | $\chi^2 = 45.4**$ |

EXAMPLE 9

Transformation of Freshly Excised Immature Embryos Relative to Pre-Cultured Embryos in Paired Comparisons Using Optimized Protocols From previous examples, fresh embryo bombardments can be used to effect stable transformation of maize. However, the method should be placed in the context of the standard protocol used to ascertain if the new method has value to logistics and throughput. Therefore, a direct comparison of the new fresh, non-induced embryo protocol with the standard induced, pre-cultured embryo method was designed and conducted.

Methods

Fresh embryos were prepared for bombardment as in Example 3 and Example 4, with no 2,4-D present pre-bombardment and modified to include those modifications to the protocol that promoted maximal transformation frequency as identified in Examples 5 through 8. Conditions included 19% sucrose present in the pre-bombardment conditioning/holding phase (modified 560Y), 0.6% Au particles, 200 psi rupture disk, and embryos targeted on shelf 2 of the Biolistics device. Embryos were bombarded as they remained flat with their embryonic axis in contact with the support medium. Plasmid vectors and 0.6μ Au particles were associated as in Example 2 and 3.

For cultured embryo bombardments, embryos from the same ears used for fresh embryo bombardments were pre-cultured on 560L medium for 4–5 days in darkness at 28° C. At this time, a small amount of incipient embryogenic tissue can be observed at the coleorhizal end of the scutellum. As preparation for bombardment, the embryos were transferred to 560Y modified to contain 19% sucrose and incubated in darkness at 28° C. for 4 hours. The embryos were arranged, 10 embryos per plate, in a 2 cm target zone. The embryos were angled with their coleorhizal end pointing up toward the macrocarrier at approximately a 300 angle. Plates of pre-cultured embryos were bombarded at shelf 2, with a 650 psi rupture disk. Plasmid vectors and 0.6μ Au particles were associated as in Example 2 and 3. This process represents the standard protocol used commonly.

The eight plasmid vectors used in this experiment possessed CaMV35S-1841:Ω':adh1$_{int}$::BAR::pinII as the selectable marker, but each varied in the composition of the proprietary agronomic gene. These vectors were labeled PHP-A, PHP-B, PHP-C, PHP-D, PHP-E, PHP-F, PHP-G, and PHP-H.

After bombardment, the embryos were handled as in Example 4 for the production of and regeneration of transgenic events.

Results

While there was construct to construct variability, pooled across the eight constructs tested, fresh embryo bombardments outperformed the standard pre-cultured embryo bombardments by about two-fold (Table 10). This difference was statistically significant. Therefore, fresh embryo bombardments can be used in production transformation in the product commercialization pathway.

TABLE 10

Transformation of Freshly Excised Immature Embryos Relative to Pre-Cultured Embryos in Paired Comparisons Using Optimized Protocols

| GENE | Embryo Treatment | |
|---|---|---|
| | Fresh Embryo Bombardment | Pre-cultured Embryo Bombardment |
| PHP-A | 0.18 | 0.12 |
| PHP-B | 0.23 | 0.071 |
| PHP-C | 0.10 | 0.10 |
| PHP-D | 0.11 | 0.17 |
| PHP-E | 0.24 | 0.12 |
| PHP-F | 0.34 | 0.15 |
| PHP-G | 0.19 | 0.075 |
| PHP-H | 0.40 | 0.13 |
| Pooled Data | 0.24 | 0.12 |

Transformation Frequency
$x^2 = 48.4**$

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for producing a maize cell in which a nucleotide of interest is stably integrated, said method comprising:
    (a) isolating at least one immature embryo from a maize ear; and
    (b) introducing a nucleotide construct into at least one cell of said immature embryo by microprojectile bombardment within 6 hours of isolating said immature embryo wherein said immature embryo does not come in contact with an external auxin before or during bombardment.

2. The method of claim 1 wherein said immature embryo comes in contact with a medium that comprises an osmotic potential greater than that produced by a medium containing 3% (w/v) sucrose.

3. The method of claim 2 wherein said medium comprises an osmoticum consisting of sucrose, sorbitol, mannitol, polyethylene glycol, or combinations thereof.

4. The method of claim 1 wherein said immature embryo does not come in contact with an external phytohormone before or during bombardment.

5. A method for producing a transgenic maize plant, said method comprising:
    (a) obtaining at least one immature embryo from a maize plant;
    (b) introducing a nucleotide construct into at least one cell of said immature embryo by microprojectile bombardment wherein introduction of the nucleotide construct occurs within 6 hours of isolating said immature embryo;
    (c) contacting said immature embryo with only an auxin-depleted transformation support medium prior to said bombardment; and
    (d) regenerating said cell into a transgenic maize plant wherein said cell comprises stably incorporated in its genome at least one copy of said nucleotide construct or part thereof.

6. The method of claim 5 wherein said auxin-depleted transformation support medium comprises an osmotic potential greater than that produced by a medium containing 3% (w/v) sucrose.

7. The method of claim 6 wherein said auxin-depleted transformation support medium comprises an osmoticum of sucrose, sorbitol, mannitol, polyethylene glycol, or combinations thereof.

8. The method of claim 5 wherein said auxin-depleted transformation support medium is phytohormone depleted.

9. The method of claim 5 wherein said immature embryo is held on said auxin-depleted transformation support medium not more than about 4 hours before said nucleotide construct is introduced.

10. The method of claim 9 wherein said immature embryo is held on said auxin-depleted transformation support medium not more than about 2 hours before said nucleotide construct is introduced.

11. A method for stable transformation of freshly excised embryos said method comprising:
    (a) obtaining at least one immature embryo from a maize plant;
    (b) introducing a nucleotide construct into at least one cell of said immature embryo by microprojectile bombardment comprising 0.6μ Au particles, rupture disk rating of about 200 p.s.i., and positioning said immature embryo between about 6 cm and about 12 cm from the macrocarrier platform wherein said microprojectile bombardment occurs within 6 hours of obtaining said immature embryo and wherein no external auxin comes in contact with the immature embryo before microprojectile bombardment is performed.

* * * * *

UNITED STATES PATENT AND TRADEMARK OFFICE
CERTIFICATE OF CORRECTION

| | | |
|---|---|---|
| PATENT NO. | : 7,057,089 B2 | Page 1 of 1 |
| APPLICATION NO. | : 09/993080 | |
| DATED | : June 6, 2006 | |
| INVENTOR(S) | : Jerome P. Ranch et al. | |

It is certified that error appears in the above-identified patent and that said Letters Patent is hereby corrected as shown below:

Column 28,
Lines 51-64 should read as follows:
-- A method for stable transformation of freshly excised embryos said method comprising:
(a) obtaining at least one immature embryo from a maize plant:
(b) introducing a nucleotide construct into at least one cell of said immature embryo by microprojectile bombardment comprising 0.6µ Au particles, rupture disk rating of about 200 p.s.i., and positioning said immature embryo between about 8 cm and about 12 cm from the macrocarrier platform wherein said microprojectile bombardment occurs within 6 hours of obtaining said immature embryo and wherein no external auxin comes in contact with the immature embryo before microprojectile bombardment is performed. --

Signed and Sealed this

Twelfth Day of December, 2006

JON W. DUDAS
*Director of the United States Patent and Trademark Office*